United States Patent [19]

Lange

[11] Patent Number: 4,826,577
[45] Date of Patent: May 2, 1989

[54] CONTROL SYSTEM FOR ELECTROCHEMICAL PROTECTION ON SUBMERSIBLE METAL STRUCTURES

[76] Inventor: Gösta Lange, Ovanskogsliden 15, Göteborg, Sweden, 416 56

[21] Appl. No.: 16,111

[22] Filed: Feb. 18, 1987

[51] Int. Cl.⁴ .............................................. C23F 13/00
[52] U.S. Cl. ................................... 204/1 T; 204/400; 204/404; 204/196; 204/147; 307/95; 340/856
[58] Field of Search ................ 204/196, 147, 1 T, 1 C, 204/400, 404; 307/95; 340/853, 856, 857, 858

[56] References Cited

U.S. PATENT DOCUMENTS

| | | | |
|---|---|---|---|
| 3,351,545 | 11/1967 | Heuze | 204/196 |
| 3,930,220 | 12/1975 | Shawhan | 367/82 |
| 3,990,478 | 11/1976 | McFarland | 204/196 |
| 4,090,170 | 5/1978 | Lincklaen-Arriens et al. | 307/95 |
| 4,178,579 | 12/1979 | McGibbeny et al. | 340/857 |
| 4,583,093 | 4/1986 | Beals | 340/857 |
| 4,584,675 | 4/1986 | Peppers | 340/853 |
| 4,631,536 | 12/1986 | Ward et al. | 340/857 |

FOREIGN PATENT DOCUMENTS 0060552 9/1985 European Pat. Off. .
3110054 10/1982 Fed. Rep. of Germany .
150969 12/1976 Norway .

*Primary Examiner*—T. Tung
*Assistant Examiner*—Stephen P. Marquis
*Attorney, Agent, or Firm*—Holman & Stern

[57] ABSTRACT

A method and device for automatic surveillance of electrochemical protection on submersible metal structures. The difference in electric potential between the steel structure and at least one electrode, in contact with the ambient water, is detected with a supply of electric alternating current, via the steel structure and a parallel, insulated conductor. The detected values are transmitted to a central monitoring unit recording said values, via said steel structure and said conductor, as a pulse coded signal, superposed upon the supply current, which acts as a system clock.

7 Claims, 1 Drawing Sheet

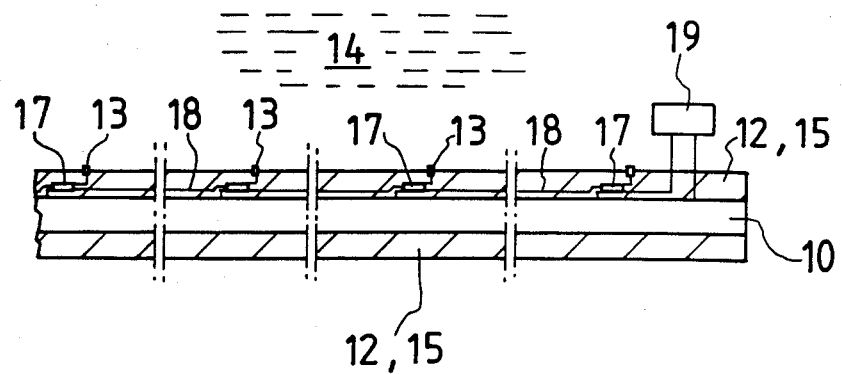
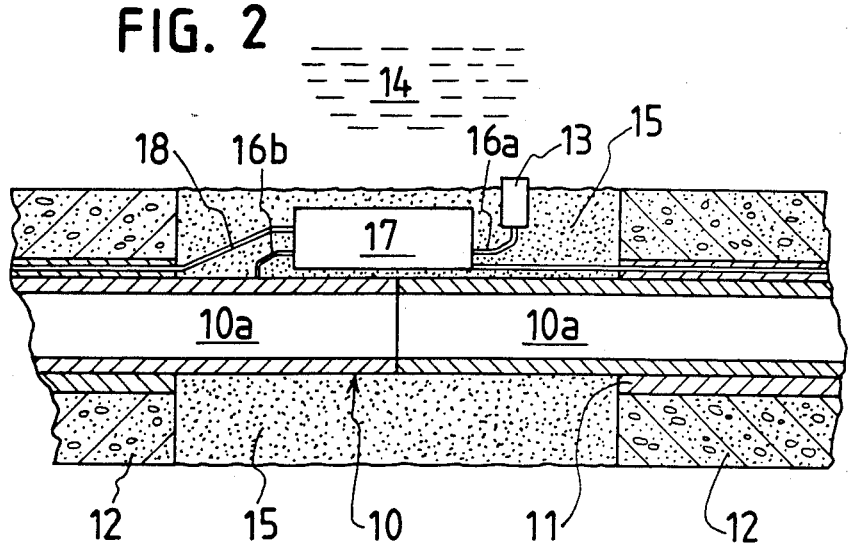

CONTROL SYSTEM FOR ELECTROCHEMICAL PROTECTION ON SUBMERSIBLE METAL STRUCTURES

FIELD OF THE INVENTION

The invention relates to a method and device for automatic surveillance of electrochemical protection on submersible metal structures, wherein the difference in electric potential between the steel structure and at least one electrode in contact with the ambient water, is detected with a supply of electric alternating current.

BACKGROUND OF THE INVENTION

There is always a risk of leakage in systems for production and distribution of liquid and gaseous fluids. A major problem here is corrosion and anodic or cathodic protection is used as corrosion protection on oil and gas pipes, onshore or offshore and also on stressed steel structures, offshore. Either this corrosion protection is produced by an electric current or by sacrificial anodes, it is vital that the protection does not degenerate as time pass. Causes for degeneration may be damages to the mechanically applied surface protection, faults in sacrificial anode systems etc.

Therefore the electrochemical protection of steel structures and pipes must be checked closely and several methods have been developed for this surveillance. Visual inspection by divers or by remotely operated vehicle and TV-camera is often used. Also detection of the electrode potential of the steel or the electric density in the ambient water. Both said methods normally require the use of supply ships, divers or robots. The necessity of making this inspection over long distances at submerged oil or gas pipes, makes each inspection very expensive since it involves large efforts in manpower and technical means at considerable risk. In case of a buried pipe, it is often not available for outer inspection.

In view of the above, a permanently installed electronic monitoring system would render several advantages in comparance with the present systems. Thus the total expenses for inspection would be considerably reduced during the lifetime of the installation; the risk for human and equipment damages would be avoided; continuous inspection is possible, and buried pipes could also be inspected. The problem so far has been to make a simple and endurable monitoring system for this environment.

SUMMARY OF THE INVENTION

The object of the present invention is to provide such a monitoring system, which is adapted to the special conditions existing, e.g. when laying pipe lines offshore.

The method according to the invention is characterized in that the current is supplied via the steel structure and a parallell, insulated conductor, that said difference in electric potential is detected by means of a transducer at each of said electrodes, which transforms said value from its electrode to a first pulse coded signal component to which is added a second pulse coded address signal, which is unique for each transducer and is used to identify the position of said value along the steel structure, and that the detected values are transmitted to a central monitoring unit recording said values, via said steel structure and said conductor, as a pulse coded signal, superposed upon the supply current, whcih acts as a system clock.

According to one embodiment of this method, the transducers are selectively activated by means of an address signal from the central monitoring unit for individual report of present potential value. Alternatively, the transducers are activated when the potential value surpasses a present limit value, for report to the central unit.

An apparatus according to the invention is characterized in that a number of electrodes are placed at intervals along the surface of the steel structure, so that they are in contact with the water and are interconnected to each other via a transducer, which communicates with a central monitoring unit via the steel structure and a parallel, insulated conductor for transmission of supply current to the transducers and detected values to said central unit, said values having their source from the difference in electric potential between the respective electrode and said surface.

BRIEF DESCRIPTION OF THE DRAWINGS

FIG. 1 is a schematic representation of a pipe-line provided with a control system according to the invention, and FIG. 2 show details in the control system in an enlarged scale.

DESCRIPTION OF A PREFERRED EMBODIMENT

In FIGS. 1 and 2 number 10 indicate the steel pipe which surface protection will be detected. The pipe is made of several welded sections 10a. Over a large part of their length, they are covered by a protective layer 11 of asphalt and over said layer an outer heavy layer 12 of concrete for negative buoyancy. An electrode 13 from other metal than steel, e.g. platinum, graphite or zinc is placed in contact with the ambient water 14. A preferable location for the electrode is in the gap existing between the concrete of two adjacent sections before this gap has been filled by a mass 15.

An electric field force is created between the steel pipe 10 and the electrode 13, which can be detected by means of a highohmic detector device. The measured field force is directly proportional to the electrochemical protection of the pipe.

In FIG. 2 is shown how the electrode 13 is connected via a short conductor 16a to an electronic transducer 17, which also is connected to the pipe 10 via a short conductor 16b. The transducer transforms the electric field force into a pulse coded modulated digital signal, wherein the pulse code has a mathematic relationship with said field force. The transducer 17 is also connected in series with a conductor 18 which runs along the entire length of the pipe. By this single conductor 18, having the pipe 10 as the second terminal, the power is supplied to the transducer 17 and the above described pulse code is transmitted to a central monitoring unit 19 (see FIG. 1) at one end of the conductor 18.

The transducer 17 is designed to receive signals from the conductor 18 and respond to these signals by sending its pulse coded signal. The operation of the complete system having any number of transducers and electrodes will now be described in the following.

For practical reasons, it is desirable that the transmission of energy and information is made via one single long conductor. In a practical realisation of the invention, one conductor section will be moulded in along one pipe section, preferably in the asphalt layer. When two pipe sections are welded together, the conductor sections are also welded together. Since there is only one conductor to splice, the time required for splicing this conductor and installing the electrodes and transducers will be minimized.

It is also desirable that the energy transmitted by the long conductor 18 mainly is composed of alternating current signals. Direct current would imply a risk for galvanic corrosion on the conductor if it cannot be guaranteed that the conductor will be completely free from moisture. In the type of environment that the invention mainly will be used in, such freedom of moisture can hardly be maintained.

FIG. 1 shows an arrangement for bidirectional communication and simultaneous supply of energy along the longitudinal conductor 18 having the steel pipe 10 as a second terminal. One end of the conductor 18 is connected to the central monitoring unit 19, which emits an alternating current. When the unit 19 wants to communicate with any of the transducers connected to the conductor 18, the voltage wave of the alternating current is pulse modulated in such way that a certain address and a message is formed.

FIG. 1 also show how a number of transducers 17 are connected to the conductor 18. Each transducer 17 has its own pulse code combination which serves both as identification sign when a message is transmitted and an address when messages are received. All message signals, either transmitted or received, are synchronized by means of said alternating current signal, which acts as a system clock.

If the conductor 18 is long or if many transducers 17 are connected, the transducers normally are standing by; i.e. they are not sending any messages, only listening drawing a minimum of energy. They can be activated either by an interrogation signal from the central 19 with a specific address to one of the transducers in the system; or they can activate themselves in case the limit value from the steel pipe 10 and the electrode 13 falls beyond a preset area of acceptable readings. When a transducer is activated in any of the above or other ways, it sends a message to the central 19 via the conductor 18. The message starts with the specific address code of the transducer 17 and continues with a report of the present status of the electric potential. This report may trigger an alarm in the central 19 and the message from the transducer 17 will be recorded.

The invention is not limited to the above described embodiment, but several variations are possible within the scope of the accompanying claims. For example, the device may be modified for use at an offshore steel construction, e.g. a fixed or floating platform for development of oil or gas. Therefore monitoring circuits may run along stressed struts or beams, and several electrodes may be connected to the same transducer, so that a medium value for the electric potential at a certain part of the structure may be detected. The control system according to the invention can be used for transmission of other information, e.g. pressure or temperature. The conductor may comprise several electric cords, running in parallel between two points for increased safety against a rupture.

I claim:

1. A method for automatic surveillance of the electrochemical protection on submersible metal structures, comprising:
   supplying alternating electric current to a submersible metal structure and to an insulated conductor connected in parallel with the metal structure, said alternating current providing a system clock;
   detecting the difference in electric potential between the metal structure and at least one electrode in contact with the ambient water, said difference being detected by a transducer means at each said electrode, each said transducer means being connected to the metal structure, to a respective electrode and to said insulated conductor;
   converting said difference in electric potential into a first pulse coded signal corresponding thereto;
   adding to said first pulse coded signal a second pulse coded address signal unique to each said transducer means for identifying the origin of said first pulse coded signal component;
   superposing said first and second pulse coded signals on said alternating electric current in synchronism therewith;
   transmitting said superposed first and second pulse coded signals along said insulated conductor; and
   receiving said superposed first and second pulse coded signals at a central monitoring unit connected to said metal structure and to said insulated conductor.

2. The method according to claim 1, further comprising maintaining said transducer means normally in an inactive stand-by state, said central monitoring unit selectively activating said transducer means by transmitting along said insulated conductor a pulse coded interrogation signal specific to said transducer means, said pulse coded interrogation signal being superposed upon and synchronized with said alternating electric current.

3. The method according to claim 1, further comprising maintaining said transducer means normally in an inactive stand-by-state, and activating said transducer means when said difference in electric potential exceeds a predetermined value limit.

4. A system for automatic surveillance of the electrochemical protection on submersible metal structures, comprising:
   power supply means operably connected to a submersible metal structure for supplying an alternating electric current thereto, said alternating current providing a system clock;
   insulated conductor means operably connected to said power supply means and in parallel connection with said submersible metal structure for constituting therewith a parallel electrical circuit carrying said alternating electric current;
   a plurality of electrodes located at intervals along said submersible metal structure, each said electrode being in contact with the ambient water;
   transducer means operably connected to said submersible metal structure and to said insulated conductor, said transducer means also being operably connected with at least one of said plurality of electrodes, said transducer means detecting the difference in electric potential between said submersible metal structure and said at least one electrode and converting said difference into an electrical signal corresponding thereto, said transducer means further superposing said signal on said alternating electric current in synchronism therewith; and a central monitoring unit operably connected to said submersible metal structure and to said insulated conductor for receiving signals from said transducer means.

5. The system according to claim 4 wherein a plurality of said transducer means are provided, each being operably connected to one or more respective ones of said plurality of electrodes, each of said transducer means detecting the difference in electric potential between a respective one of said electrodes and said submersible metal structure and transmitting the value of said detected difference along said insulated conductor as a first pulse coded signal corresponding to said value and a second pulse coded signal specific to said respective transducer means, said first and second pulse coded signals being superposed on said alternating electric current in synchronism therewith.

6. The system according to claim 5 wherein each of said transducer means is normally maintained in an inactive stand-by state, each said transducer means being activated by a pulse coded interrogation signal specific thereto transmitted along said insulated conductor from said central monitoring unit, said interrogation signal being superposed on and synchronized with said alternating electric current.

7. The system according to claim 8 wherein each of said transducer means is normally maintained in an inactive stand-by state, each said transducer means being activated when the difference in electric potential between said submersible metal structure and a respective one of said electrodes connected to said transducer means exceeds a predetermined limit value.

* * * * *